United States Patent
Dingler et al.

[19]

[11] Patent Number: 5,911,736
[45] Date of Patent: Jun. 15, 1999

[54] ENDOSCOPIC INSTRUMENT

[75] Inventors: Andreas Dingler, Birkenfeld; Ernst Falk, Sternenfels-Diefenbach, both of Germany

[73] Assignee: Richard Wolf GmbH, Knittlingen, Germany

[21] Appl. No.: 09/176,350

[22] Filed: Oct. 21, 1998

[30] Foreign Application Priority Data

Oct. 24, 1997 [DE] Germany .......................... 197 47 043

[51] Int. Cl.$^6$ ................................................. A61B 17/28
[52] U.S. Cl. ......................................................... 606/208
[58] Field of Search ........................... 606/208, 205–207, 606/174–175, 167; 30/340–341, 260, 335–337

[56] References Cited

U.S. PATENT DOCUMENTS

| 5,263,967 | 11/1993 | Lyons, III et al. | 606/205 |
| 5,810,865 | 9/1998 | Koscher et al. | 606/174 |
| 5,830,231 | 11/1998 | Geiges, Jr. | 606/205 |

FOREIGN PATENT DOCUMENTS 0 537 574 A2   4/1993   European Pat. Off. .

*Primary Examiner*—Michael Buiz
*Assistant Examiner*—Vikki Trinh
*Attorney, Agent, or Firm*—Cohen, Pontani, Lieberman & Pavane

[57] ABSTRACT

The endoscopic instrument comprises two working parts provided at the distal end region of an elongate shank, of which at least one is pivotingly movable relative to the other, and is provided with handle at the proximal end region of the shank for actuating at least one of the working parts via an actuation rod running in the shank, wherein the working parts in the region of their pivoting mounting submit to a spring force for pressing these parts onto one another. For achieving an exact bearing force of the working parts on one another and an increased security against their damage during use of the instrument the shank at its distal end is provided with a fork-shaped holder with two resilient distal fork arms producing the pressing force onto the working parts, whose at least one fork arm comprises a receiver bore. The pivotingly movable working part is inserted in the intermediate space formed by the two fork arms and is provided with a projecting joint peg which pivotingly engages into the receiver bore of the allocated fork arm of the holder.

8 Claims, 2 Drawing Sheets

ENDOSCOPIC INSTRUMENT

BACKGROUND OF THE INVENTION

The invention relates to an endoscopic instrument which at the distal end region of an elongate shank comprises two working parts of which at least one is pivotingly movable relative to the other, and at the proximal end region of the shank is provided with a handle for actuating at least one of the working parts via an actuation rod running in the shank, wherein the working parts in the region of the pivoting mounting are submitted to a spring force for pressing apart these parts.

Such an endoscopic instrument is described in EP-0 537 574 A2. It may be formed for example as a pair of scissors blades wherein the one of the blades or cutting parts is mounted in a pivotingly movable manner by way of an axle pin, while the other blade or cutting part is stationary. So that all blade or cutting parts acting as working parts during the complete cutting procedure remain in firm contact with one another over their whole working length, that is to say are pressed on one another, a disk spring or plate spring is mounted on the axle pin outside the working parts, with whose force the two working parts are pressed onto one another. With this instrument there is the disadvantage that the pressing force of the spring acting on the two working parts can only be set roughly and with difficulty since the calculated dimensions for the axle pin and the pressing spring on account of the manufacturing and assembly tolerances for these parts with which tissue of a patient is to be gripped and/or cut, after their assembly, mostly have not led to the desirable value of the required pressing force for the working parts. Thus the endoscopic instrument cannot be applied to the same degree to soft or harder tissue, for example cartilage tissue. If the result of the assembly is a relatively strong pressing force then the instrument is not suitable for cutting soft tissue since it may not be delicately handled, and vice versa. A further considerable disadvantage with the prior known instrument lies in the fact that it only has a slight safety against overloading which is determined by the height, which cannot be changed, of the plate spring which is pretensioned in the assembled condition and is seated on the axle pin. By way of this the working parts, on cutting the thick and gristly tissue of a patient, may only give slighly along the axle pin. Therefore, in particular with an instrument with a low pressing force of the working parts onto one another there exists the extremely premature danger of the instrument, with overloading at least in the region of the cutters of the working parts, being damaged by the bending of these parts. Furthermore with the known instrument it is disadvantageous that the assembly of the working parts by way of an axle or linkage pin and a plate spring or spring disk by way of a rivetting procedure is relatively time consuming and complicated in manufacture with the associated manufacturing costs.

BRIEF SUMMARY OF THE INVENTION

It is an object of present invention to improve the endoscopic instrument of the previously cited type such that with a simplified and cheaper assembly of the working parts of the instrument, the bearing of these parts on one another over their complete working length with a precalculated, constant pressing force is essentially ensured and that there is an increased safety of the working parts against overloading.

This object is achieved by an endoscopic instrument comprising two working parts provided at the distal end region of an elongate shank, of which at least one is pivotingly movable relative to the other, and a handle provided at the proximal end region of the shank for actuating at least one of the working parts via an actuation rod running in the shank, wherein the working parts in the region of their pivoting mounting submit to a spring force for pressing these parts onto one another, wherein the shank at its distal end is provided with a fork-shaped holder with two resilient, distal fork arms producing the pressing force onto the working parts, whose at least one fork arm comprises a receiver bore, wherein the pivotingly movable working part is inserted in the intermediate space formed by the two fork arms is provided with a projecting joint peg which pivotingly engages into the receiver bore of the allocated fork arm of the holder, and wherein the other working part is connected in the same manner or rigidly to the other fork arm.

Instead of the application of a plate spring or spring disk there is provided a fork-shaped holder which is mounted at the distal end of the endoscope and which comprises two distal spring-elastic fork arms with a predetermined pressing force for the working parts, for example scissor cutting parts. Steel is used is a material for the fork-shaped holder or its fork arms so that the fork arms essentially in combination with their length and their position to one another exert a predetermined pressing force from outside onto the working parts if these are mounted in the intermediate space between the fork arms. Furthermore an axle pin for the pivoting mounting of the working part or parts is done away with since instead of this on the working part or parts a peg projection or peg projections are provided which freely rotatably engage into corresponding holes in the distal end regions of the fork arms and in a simple manner effect a positional fixation for the working parts. All components may be manufactured with little cost. They may also be simply assembled in that the fork arms are spread apart far enough for the working parts with their peg projection to be able to be inserted into the corresponding hole of the fork arm. On springing back of the fork arms these bear on the working parts with the precalculated pressing force. Thus the fork arms not only assume the holding function of the conventional axle pin but at the same time also the function of the desired pressing force. Furthermore the instrument according to the invention also has an increased security against overloading of the working parts. These, on account of the lateral elasticity of the fork arms, may be spread apart much further than previously, wherein this spreading is only limited by the elasticity of the fork arms. Remaining deformations of the working parts are thus largely avoided.

According to one advantageous formation of the instrument in accordance with the present invention by way of a selection of the dimensions and of the smallest distance of the fork arm or fork arms of the holder, which hold a pivotingly movable working part and consist of resilient material, a predetermined pressing force of the fork arm or fork arms on the working part allocated to it or them may be co-determined. By way of this the pressing force in each case for the working parts may be exactly set in the simplest manner.

A further advantageous formation feature for the instrument according to the present invention lies in the fact that each pivotingly movable working part and its projecting joint peg are formed as a one-piece component. By way of this the assembly of a separate joint peg on the working part is done away with.

BRIEF DESCRIPTION OF THE DRAWINGS

The invention is hereinafter described in more detail by way of an embodiment example shown in the accompanying drawings. There are shown.

DETAILED DESCRIPTION OF THE INVENTION

Figure 1:
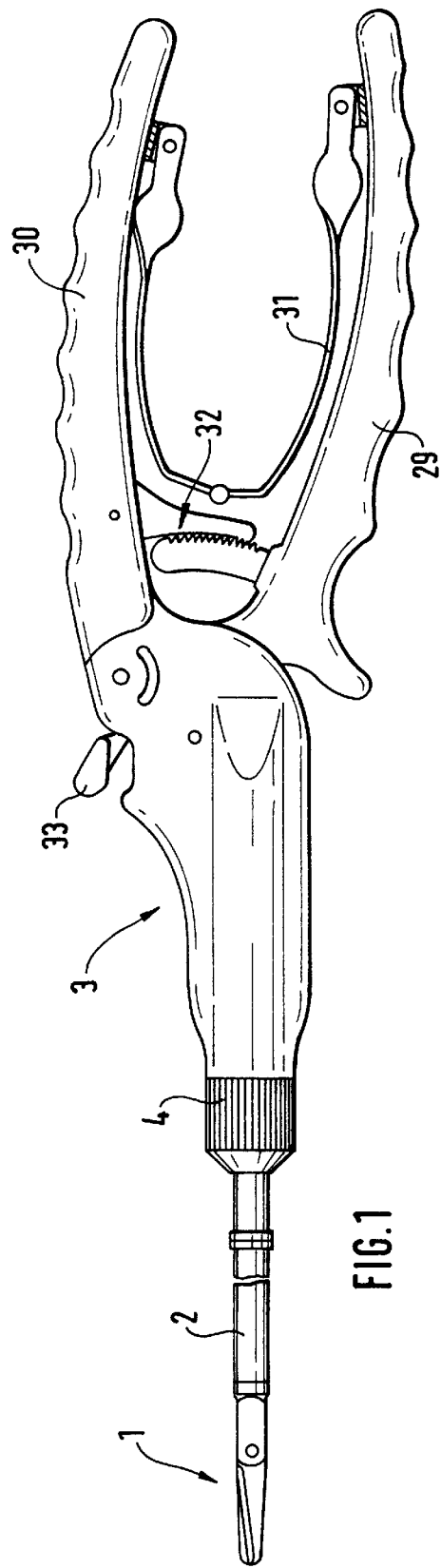
FIG. 1 a lateral view of the embodiment example.

The endoscopic instrument which is shown completely in FIG. 1 comprises a distal working unit 1, an elongate hollow shank 2 and a proximal actuation handle 3, wherein the shank 2 and the handle 3 which are connected to one another via a connection sleeve 4 are of a conventional constructional type and are therefore not described in any detail. The working unit 1 may be a scissor unit as is for example shown. The working unit 1 in another embodiment is a forceps unit whose active forceps parts may be formed in the most comprehensive shape corresponding to the respective application purpose, as is generally known. Thus in this case it may for example be the case of a gripping forceps unit. The working unit 1 applied in each case is distally releasably connected to the hollow shank, and thus may be easily exchanged in the case of repair or maintenance. A changing of the working unit 1 in each case by way of the operating physician is effected in that the larger unit formed by the unit 1 and the shank 2 is separated by the physician by actuation of the screwably formed connection sleeve 4.

Figure 2:
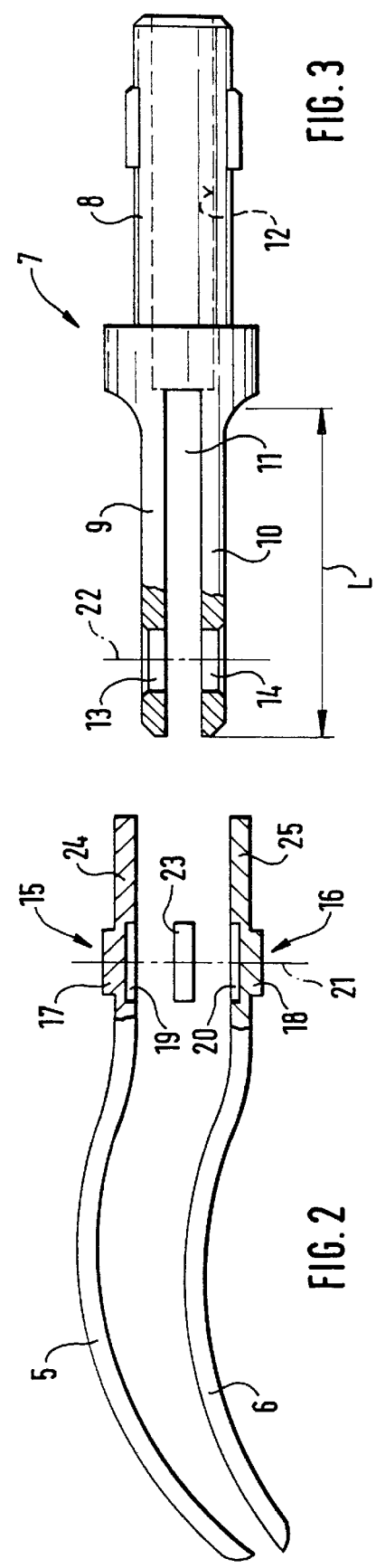
FIG. 2 an enlarged representation of two working parts.

The working unit 1 represented as a scissors in FIGS. 1 and 2 comprises two cutting working parts 5 and 6 which are mounted in a fork-shaped holder 7 in a pivotingly movable manner. According to FIGS. 2, 3 and 4, both working parts 5 and 6 are mounted in the fork shaped holder 7 in a pivotingly movable manner. However it is also possible that only one of the working parts 5, 6 is pivotingly movably connected to the fork shaped holder 7, whilst the other working part is rigidly connected to the holder 7.

The fork shaped holder 7 comprises a cylindrical connection part 8 for the releasable connection of the working unit 1 to the shank 2 of the endoscopic instrument and two distal fork arms 9 and 10 which extend in the longitudinal direction of the connection part 8 or the shank 2 and between them form an intermediate space. The holder 7 has an axial passage 12 for the operating rod of the proximal handle 3 in order to be able to actuate the working parts 5 and 6.

The fork shaped holder 7 and in particular the distal fork arms 9 and 10 consist of resilient material, for example metal or in particular steel or a steel alloy. Each of the resilient fork arms 9 and 10 comprise in their distal end region a receiver bore 13, 14 for the rotational bearing of the associated working part 5 and 6 respectively, as will become clear. The dimensions of the fork arms 9, 10 with respect to their length L and their cross section are so predetermined in combination with the elasticity of the material selected in each case for the fork arms 9, 10 or the holder 7, that in the region of the receiver bores 13 and 14 a desired pressing force of the fork arms 9, 10 is exerted onto the working parts 5, 6 mounted in the intermediate space 11 of these arms and on these. The intermediate space 11 of the fork arms 9, 10 at least in the region of the receiver bore 13 and 14 is dimensioned in a width and a distance from one another such that a transverse axial pressure is exerted onto the joint regions of the working parts 5, 6. A considerable factor on fixing the desired pressing force of the fork arms 9, 10 onto the working parts 5, 6, apart from the material elasticity of the fork arms, 9, 10 include the cross section of the bearing fork arms and the width of the intermediate space 11 that lies between them in the length L of the fork arms. By way of a suitable choice of the length L of the fork arms the desired pressing force in each case may be predetermined in an sensitive manner.

The working parts 5, 6 comprise in their joint region 15, 16 each an outwardly projecting joint pegs 17, 18 which preferably are formed as one piece with the working parts 5, 6 and from the inside pivotably engage into the receiver bores 13, 14 of the fork arms 9, 10 of the fork shaped holder 7. For certain cases of application it may be sufficient for the working parts 5, 6 apart from their joint pegs 17, 18 not to comprise a further formation and thus on the one hand are pivotably mounted with their joint pegs in the receiver bores 13, 14 of the holder 7 and on the other hand bear loosely on one another but pressed against one another.

Figure 3:
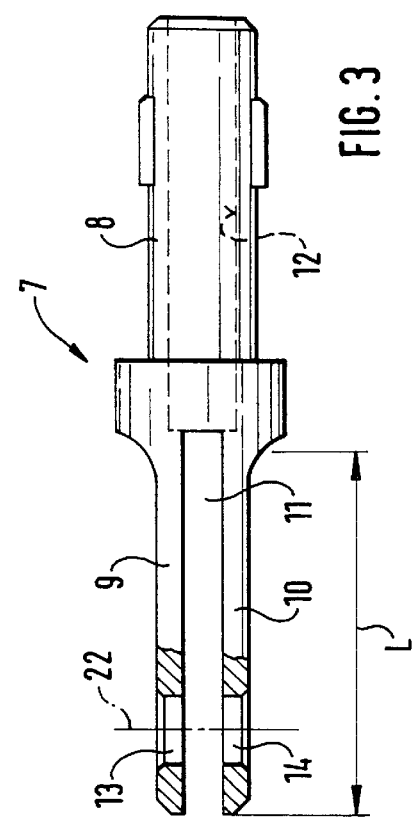
FIG. 3 an enlarged representation of a fork-shaped holder for the working parts according to FIG. 2, FIG. 4 the working parts and the holder according to the FIGS. 2 and 3 in the assembled condition.

In an advantageous further embodiment of the joint regions 15, 16 of the working parts 5, 6 in each joint region 15, 16 deepenings 19 and 20 are respectively provided, specifically on the inner side of the working parts 5, 6 in a manner such that the deepenings lie opposite the joint pegs 17, 18 on the inner side, wherein the joint pegs 17, 18 and the deepenings 19, 20 lie on a common pivoting axis 21 which in the assembled condition of the working parts 5, 6 runs through the center point of the receiver bores 13, 14 of the fork shaped holder 7, which is indicated in FIG. 3 by the dot-dashed line 22. Furthermore a common inner support piece 23 is provided which in the assembled condition of the working parts 5, 6 sits loosely in the deepenings 19, 20 as can be best recognized from FIG. 4. Additionally the working parts 5, 6 are loosely rotatably supported on this support piece 23. Advantageously the deepenings 19, 20 and the common support piece 23 are formed circular. However other shapes are also conceivable wherein it must only be ensured that the working parts may pivot against one another in a securely guided manner. The deepening 19, 20, support pieces 23 thus form a positive fit joint guide for the working parts 5, 6 which by way of this are additionally pivotingly stabilized in their length.

In another embodiment of the invention of the previously described positive fit joint guide may be proceeded such that only one of the working parts is provided with an inner-side deepening whilst the other working part comprises an inner projection corresponding to the support pieces 23 which then engages into the deepening of the working part lying opposite.

Assembling the working parts 5, 6 on the holder 7 proceeds as follows. After the working parts 5, 6 are placed against one another on the common axis line 21 while applying the support piece 23 into one of the deepenings 19 or 20, the longitudinal axial fork arms 9, 10 of the holder 7 are spread apart so far that the working parts 5, 6 with their joint pegs 17, 18 are inserted between those of the fork arms 9, 10. After inserting the working parts the 5, 6 fork arms 9, 10 are again eased. With this the joint pegs 17, 18 loosely engaged into the receiever bores 13, 14. In this assembled condition the working parts 5, 6 bear on the common support piece 23, this being by the transverse axial pressing force of the resilient fork arms 9, 10 which laterally press against the working parts with a predetermined force in the joint regions 15, 16 of the working parts 5, 6.

The further construction of the endoscopic instrument is generally known and does not form the subject-matter of the invention. It is therefore only briefly described.

Figure 4:
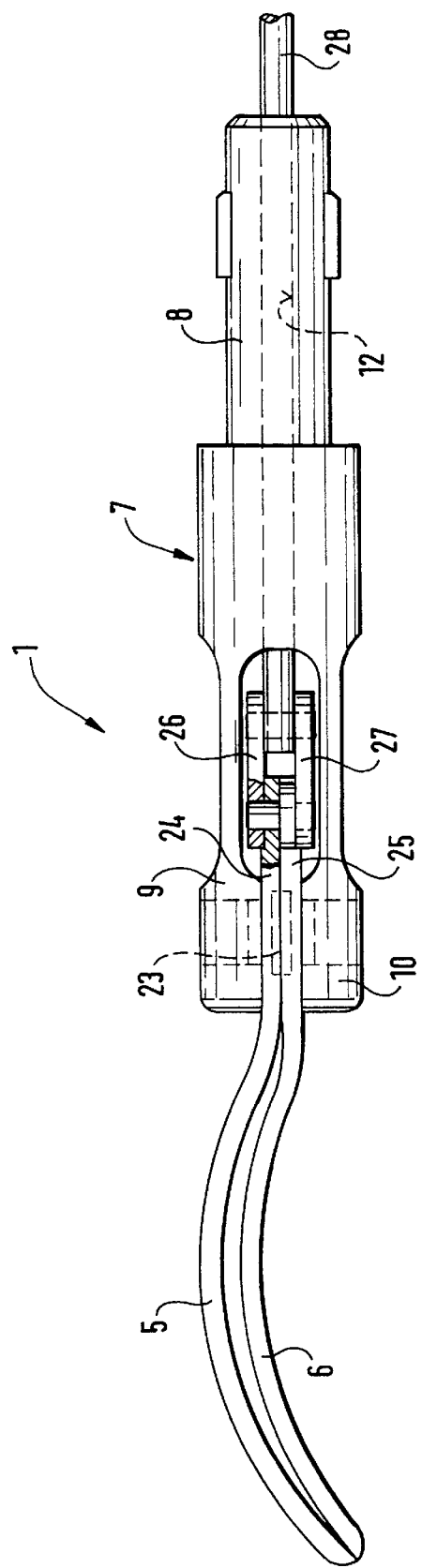

As can be recognized from FIG. 4 the proximal-side sections 24 and 25 of the working parts 5 and 6 respectively are connected to a linkage system comprising joint tabs 26, 27 which in turn are connected to an actuation rod 28 running through the passage 12 of the holder 7. This rod 28 is connected to the pivotable lever 29 of the handle 3 and by way of the pivoting of this is axially moved by which means the working parts 5, 6 open and close. The handle 3 further comprises an unmovable holding arm 30 which lies opposite the moving lever 29. Further there is provided a spring means 31 acting between the parts 29 and 30, which normally keeps the lever 29 in its open position. With the lever 29 pressed together a blocking means 32 located between the parts 29 and 30 has the effect that the working parts 5, 6 likewise are located in a closer position to one another or are located in the closed position. With an auxiliary lever 3 of the handle 3 the blocking means 32 can again be unlocked by which means the working parts 5, 6 open again.

On account of the previously described rotational mounting of the working parts 5, 6 on the resilient fork arms 9, 10 of the holder 7, the danger that the working parts, in particular the blades thereof when using the working parts as a scissors, or that the whole working unit 1 when not using the working unit or endoscopic instrument as directed, become damaged or destroyed is avoided or at least considerably reduced. This is particularly the case when harder tissue, for example cartilage tissue of a patient is to be treated. Furthermore with the instrument described, a more sensitive treatment of tissue in a large scope may be carried out, by which means a frequent change of instrument is avoided because with the instrument described tissue of differing hardness may be treated to an equal degree.

We claim:

1. An endoscopic instrument comprising:
    an elongate shank having a distal end region and a proximal end region, the distal end region being fork-shaped and having first and second resilient fork arms forming an intermediate space therebetween, the first resilient fork arm comprising a receiver bore;
    an actuation rod in the elongate shank;
    first and second working parts provided at the distal end region of the elongate shank, at least the first working part being pivotingly mounted and movable relative to the second working part; and
    a handle provided at the proximal end region of the elongate shank for actuating at least one of the working parts via the actuation rod in the elongate shank,
    the first and second resilient fork arms producing a pressing force on the first and second working parts in a region of their pivoting mounting,
    the first working part being provided with a projecting joint peg, the first working part being inserted in the intermediate space formed by the first and second resilient fork arms, and the projecting joint peg pivotingly engaging into the receiver bore of the first resilient fork arm.

2. The endoscopic instrument according to claim 1, wherein a predetermined pressing force of the first and second fork arms on the first and the second working parts is determined by the dimensions of the first and second fork arms and the distance of the first fork arm from the second fork arm.

3. The endoscopic instrument according to claim 2, wherein the pressing force of the first and second fork arms is determined by their length.

4. The endoscopic instrument according to claim 1, wherein the projecting joint peg and the first working part are formed as a one piece component.

5. The endoscopic instrument according to claim 1, wherein the second working part is pivotingly movably connected to the second resilient fork arm, and wherein the first and second working parts are pivotingly stabilized by a positive fit joint guide on a common transverse axis.

6. The endoscopic instrument according to claim 5, wherein the positive fit joint guide consists of two circular deepenings formed opposite the projecting joint peg in the first and second working parts, the two circular deepenings being flush with one another, and of a common support piece sitting loosely in both circular deepenings, the positive fit joint guide driving the first and second working parts.

7. The endoscopic instrument according to claim 1, wherein the second working part is connected rigidly to the second resilient fork arm.

8. The endoscopic instrument according to claim 1, the second resilient fork arm comprising a second receiver bore, the second working part being provided with a second projecting joint peg, the second working part being inserted in the intermediate space formed by the first and second resilient fork arms, and the second projecting joint peg pivotingly engaging into the second receiver bore of the second resilient fork arm.

* * * * *